United States Patent
Wijesekera et al.

(10) Patent No.: US 6,388,144 B1
(45) Date of Patent: May 14, 2002

(54) METHOD FOR REDUCING METHYLBENZOFURAN LEVELS IN HIGH PURITY PHENOL

(75) Inventors: Tilak P. Wijesekera, Boothwyn, PA (US); Scott R. Keenan, Marlton, NJ (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 0 days.

(21) Appl. No.: 09/882,447

(22) Filed: Jun. 15, 2001

(51) Int. Cl.$^7$ .................................................. C07C 37/68
(52) U.S. Cl. ........................ 568/754; 568/749; 568/758
(58) Field of Search ................................ 568/754, 749, 568/758

(56) References Cited

U.S. PATENT DOCUMENTS

| | | |
|---|---|---|
| 3,029,294 A | 4/1962 | Keeble et al. |
| 3,454,653 A | 7/1969 | Larson et al. |
| 3,692,845 A | 9/1972 | Cheema et al. |
| 3,810,946 A | 5/1974 | Yeh et al. |
| 4,298,765 A | 11/1981 | Cochran et al. |
| 4,634,796 A | 1/1987 | Suciu et al. |
| 4,857,151 A | 8/1989 | Suciu et al. |
| 5,064,507 A | 11/1991 | O'Donnell et al. |
| 5,198,591 A | 3/1993 | Kiedik et al. |
| 5,264,636 A | 11/1993 | Shirahata et al. |
| 5,414,154 A | 5/1995 | Jenczewski et al. |
| 5,502,259 A | 3/1996 | Zakoshansky et al. |

FOREIGN PATENT DOCUMENTS

| | | |
|---|---|---|
| DE | 1668952 | 9/1967 |
| DE | 134427 | 2/1979 |

OTHER PUBLICATIONS

"Solid superacid catalysts", Misono, et al., Chemtech, Nov. 1993.

"Sulphonic acid cation-exchangers as catalysts in the refining of phenol and aromatic hydrocarbons", Zieborak, et al. Chemistry and Industry, Jul. 4, 1983.

*Primary Examiner*—Alan Siegel
(74) *Attorney, Agent, or Firm*—Robert A. Koons, Jr. Esq.; Matthew P. McWilliams; Buchanan Ingersoll P.C.

(57) ABSTRACT

A process for treating phenol with a strong acid ion exchange resin to reduce the level of methylbenzofuran is provided. The process is capable of being carried out at elevated temperatures for extended periods, such that cooling of the phenol from distillation temperatures prior to the resin treatment is not required. The process can reduce or eliminate the substantial costs associated with conventional processes that require cooling and re-heating the phenol.

11 Claims, No Drawings

METHOD FOR REDUCING METHYLBENZOFURAN LEVELS IN HIGH PURITY PHENOL

FIELD OF THE INVENTION

The present invention relates generally to the production of high purity phenol. More particularly, the present invention relates to a method for the reduction of methylbenzofuran levels in phenol to obtain desired high purity.

BACKGROUND OF THE INVENTION

The process commonly practiced for the production of phenol involves the oxidation of cumene to cumene hydroperoxide, followed by its acid catalyzed decomposition to phenol and acetone. Isolation of phenol from the reaction product involves a series of distillation and separation steps. The lower boiling components such as acetone, unreacted cumene as well as α-methylstyrene (AMS) are first recovered from the crude product by distillation. The remaining material is introduced into a phenol recovery column in which phenol is distilled away from the higher boiling impurities. Depending on the distillation procedures used to recover acetone, cumene and AMS, the distilled phenol may contain minor quantities of impurities such as mesityl oxide (MO), acetol (hydroxyacetone) and other aliphatic carbonyl compounds, olefinic compounds, acetophenone, cumylphenols and 2- and 3-methylbenzofuran (MBF) in addition to residual amounts of acetone, cumene and AMS. Such impurities are undesirable in phenol used in certain applications such as in the manufacture of bisphenol-A.

MBF is a particularly undesirable contaminant of phenol that is used for certain applications such as in the production of bisphenol-A, a precursor to polycarbonate resins. Due to similar volatility, MBF cannot be separated from phenol by fractional distillation. U.S. Pat. Nos. 5,064,507 and 4,857,151 describe a process of distillation in the presence of water (also called steam stripping) to reduce MBF in phenol. However, due to the high energy costs and the necessity to use large distillation columns, this process is expensive in terms of capital investment and operating costs. U.S. Pat No. 5,414,154 describes the use of a strong acid ion exchange resin to reduce the level of MBF by converting it to higher boiling compounds. U.S. Pat. No. 5,414,154 also showed that the effectiveness of MBF removal by resin treatment increases with an increase in temperature.

Although strong acid ion exchange resins also remove carbonyl compounds from phenol on contact, acetol reacts with phenol to produce more MBF. U.S. Pat. No. 5,414,154 teaches the necessity to remove acetol from phenol (e.g. by treatment with an amine) prior to contact with the resin to remove MBF.

A disadvantage of the current known methodology using an ion exchange resin to remove MBF and other minor impurities from phenol, is the temperature range utilized. German Patent 1 668 952 discusses using two similar acidic ion-exchange resins, AMBERLYST® 15 and AMBERLITE® 200 to remove carbonyl compounds from phenol at temperatures up to 200° C. However, in the examples provided, the highest temperature attained was 145° C., using a small batch of phenol with a short residence time over the resin. Further, the manufacturers' recommended maximum operating temperature to avoid degradation of the resin during extended use is usually less than about 130° C. To adhere to manufacturers suggested temperatures for avoiding degradation during extended use in commercial processes requires that phenol, distilled away from the high boiling impurities generally at temperatures above 150° C., be cooled to an appropriate temperature (80°–115° C.) prior to contact with the resin to remove MBF. Furthermore, once treated, the phenol has to be reheated to distill it from the high boiling impurities formed. This cooling and re-heating increases the time and energy costs associated with the current known resin treatment of phenol. Therefore, when applied to commercial processes where large volumes are processed, the lower maximum operating temperature of ion-exchange resins introduces several disadvantages compared with other acidic catalysts available to remove reactive organic impurities from phenol. Consequently, ion exchange resins are usually avoided as acid catalysts if higher operating temperatures are desired.

Other, high temperature stable, acidic catalysts are known for reducing organic impurities in phenol. U.S. Pat. No. 3,454,653 describes using synthetic silica-alumina catalysts for MBF removal, at temperatures above 150° C. U.S. Pat. No. 5,502,259 describes the use of medium and large pore zeolites to effectively remove MO, acetol and other carbonyl compounds as well as AMS and other unsaturated compounds from phenol. Although the catalyst is stable at higher operating temperatures (180°–200° C.), it is unable to reduce the MBF content of phenol. U.S. Pat. No. 5,264,636 describes the use of an acidic γ-alumina catalyst to selectively convert aliphatic and aromatic carbonyl compounds into higher boiling compounds without causing substantial formation of dimers of AMS. Although the catalyst was stable at operating temperatures of 280° C., it was not effective in reducing the MBF content in phenol; rather, it increased the MBF.

Accordingly, there is need for a method of using a strong acid ion exchange resin for reducing the level of impurities in phenol that reduces the level of methylbenzofuran and also is capable of being operated for extended periods at temperatures that do not require cooling of the phenol prior to treatment.

SUMMARY OF THE INVENTION

The present invention provides a method for reducing the level of impurities in phenol, which reduces the level of methylbenzofuran in phenol and operates for extended periods at temperatures that do not require cooling of the phenol prior to treatment.

In accordance with one embodiment of the present invention, a superior process for the reduction of impurities, including methylbenzofuran (MBF) in phenol is provided. Phenol is treated with an acidic ion-exchange resin at temperatures above about 130° C., preferably above about 150° C., to form higher boiling impurities. The phenol is then distilled to separate it from the higher boiling impurities formed. This increases the efficiency of the process, and eliminates the utility costs in a commercial operation. Preferably, it is recommended that prior to resin treatment, the acetol content of phenol be reduced by known methods, such as by treatment with an amine, such as Dytek-A.

DETAILED DESCRIPTION OF PREFERRED EMBODIMENTS OF THE INVENTION

The present invention provides a process for purifying phenol obtained by the acid catalyzed decomposition of cumene hydroperoxide, which in turn is obtained by the air oxidation of cumene. The process is capable of being run continuously for long periods as required in commercial processes. The crude product of the acid catalyzed decomposition of cumene hydroperoxide is first subjected to a series of distillations in order to recover acetone (co-product) cumene (unreacted starting material) and other valuable by-products such as α-methylstyrene (AMS). Distillation of the remaining material produces phenol, which contains several reactive organic impurities, including MBF, AMS, mesityl oxide, and other unsaturated compounds and aliphatic carbonyls, including acetol, which in turn, would produce more MBF when in contact with acid. The process described herein uses a strong acid ion-exchange resin to remove such reactive impurities and produce high purity phenol suitable for special applications.

Examples of ion exchange resins useful for the process described herein include styrene-divinylbenzene polymers containing aromatic sulfonic acid groups. These ion exchange resins are available in two types, macroreticular and gel types. Examples of commercially available aromatic sulfonic acid resins include, but are not limited to: AMBERLYST® A-15, AMBERLYSTO A-36 and AMBERLYST® XE-737 from Rohm and Haas Company, PUROLITE®CT-251 from Purolite, and LEWITAT® K2431 from Bayer AG. The preferred operation procedure for purification is to pass phenol containing the reactive impurities through a bed of an acid ion exchange resin maintained at the desired temperature. The purification can be carried out at a temperature above about 130° C. More preferably, the purification is carried out above about 150° C. The flow rate of phenol through the resin bed is measured as bed volumes/hour, where a bed volume is the volume of phenol equivalent to the volume of the resin bed. The flow rate is inversely proportional to the contact time. For example, a flow rate of 4 bed volumes/hour will provide a contact time of 0.25 hour. The purification can be carried out effectively at flow rates below about 12 bed volumes/hr(BV/hr), preferably from about 4 to about 8 bed volumes/hr. The phenol can be analyzed for MBF and other minor impurities (when present in concentrations >1 ppm) before and after resin treatment using gas chromatography. Preferably, prior to resin treatment, the acetol content in phenol is reduced by conventional methods such as reacting the phenol with an aliphatic amine. Most preferably, the acetol content is reduced to less than 1ppm by treatment with an aliphatic amine.

EXAMPLE 1

Purified phenol, containing 40 ppm MBF, <1 ppm acetol and <100 ppm total GC detectable impurities including carbonyls, was passed through a bed of AMBERLYST® A-36 ion exchange resin. The temperature of the bed was maintained at 148° C.–151° C. and the phenol flow rates were varied between 3.5 and 8.2 bed volumes/hr (BV/hr.). The results of these experiments are summarized in TABLE 1. The phenol effluent from the bed had the level of and total carbonyls each reduced to <1 ppm.

TABLE 1

Effect of Temperature and Flow Rates on MBF Removal Using Amberlyst 36 (MBF in Effluent - ppm)

| T (° C.) | 3.5 BV/hr | 5.7 BV/hr | 6.5 BV/hr | 7.8 BV/hr | 8.2 BV/hr |
|---|---|---|---|---|---|
| 148 | | | <1 | | |
| 149 | | <1 | | | |
| 150 | <1 | | <1 | | <1 |
| 151 | | | | <1 | |

EXAMPLE 2

A series of experiments were carried out as described in Example 1, at similar temperatures and flow rates. The phenol feed contained, in addition to 42 ppm MBF, <1 ppm acetol, 82 ppm acetone, 19 ppm MO, 48 ppm AMS and <100 ppm of other impurities. The results of these experiments are summarized in TABLE 2. The phenol effluent from the resin bed showed MBF≦3 ppm, acetone and AMS<1 ppm, MO from 4 to <1 ppm, in addition to AMS dimers, p-cumylphenol and other AMS condensation products.

TABLE 2

Effect of Temperature and Flow Rates on MBF Removal Using Amberlyst 36 (MBF in Effluent - ppm)

| T (° C.) | 4.6 BV/hr | 4.9 BV/hr | 5.3 BV/hr | 6.4 BV/hr | 6.6 BV/hr |
|---|---|---|---|---|---|
| 144 | <1 | | | | |
| 150 | <1 | | | 3 | 3 |
| 151 | | <1 | <1 | | |
| 152 | | | | | 3 |
| 153 | | | | 3 | <1 |

EXAMPLE 3

A series of experiments were carried out as described in Example 1, the resin bed temperature at 149° C.–153° C. but at flow rates between 4.5 and 10.5 BV/hr. A total of about 2500 bed volumes of phenol containing 100 ppm acetone, 157–162 ppm MBF and <1 ppm acetol, AMS and carbonyl compounds were passed. The results of these experiments are summarized in TABLE 3. The phenol effluent from the bed had approximately 85–90% of the MBF removed, and had <1 ppm acetone.

TABLE 3

Effect of Temperature and Flow Rates on MBF Removal Using Amberlyst 36

MBF (Feed/Effluent) - ppm

| T (° C.) | 4.5 BV/hr | 5.1 BV/hr | 5.8 BV/hr | 6.0 BV/hr | 6.6 BV/hr | 7.2 BV/hr | 7.9 BV/hr | 8.2 BV/hr | 8.8 BV/hr | 9.6 BV/hr | 9.8 BV/hr |
|---|---|---|---|---|---|---|---|---|---|---|---|
| 149 | | | | | | | | | 159/24 | | 157/25 |
| 150 | | | | | 160/22 | | 160/22 | 159/25 | | | |
| 151 | | | 160/20 | | | | | | | 162/26 | |
| 152 | | | | 157/20 | | | | | | | |
| 153 | 160/19 | 160/19 | | | | 160/21 | | | | | |

EXAMPLE 4

Phenol containing 40 ppm MBF, <1 ppm acetol, and <50 ppm of other impurities was passed through a bed of Amberlyst® XE-737 ion exchange resin. The MBF remaining in the eluted phenol (in ppm), at varying temperatures and flow rates in BV/hr. is given in TABLE 4. The efficiency of MBF removal increased as the temperature was raised from about 118° C. to about 152° C. The resin showed little sign of degradation above 140° C., with minimal gas evolution.

With phenol feeds containing higher MBF content (150–160 ppm), the resin removed 80–85% MBF during the passage of about 1200 bed volumes of phenol.

TABLE 4

Effect of Temperature and Flow Rates on the Removal of MBF (in ppm) from Phenol Using Amberlyst XE737 Ion Exchange Resin

| T (°C.) | Flow Rate, Bed Volumes/hr. | | | | | | | | |
|---|---|---|---|---|---|---|---|---|---|
| | 3.1 | 4.0 | 4.6–4.8 | 5.0–5.3 | 5.8–5.9 | 6.4–6.7 | 9.9–10.0 | 10.5 | 11.4 |
| 118–120 | <1 | | <1 | | | | | | |
| 121–123 | | | <1 | <1 | <1 | <1 | | | |
| 130–135 | | <1 | <1 | | <1 | | | | |
| 140–145 | | | <1 | <1 | | | | | |
| 150–152 | | | <1 | <1 | | <1 | <1 | <1 | <1 |

EXAMPLE 5

Phenol containing 40 ppm MBF, <1 ppm acetol, and <50 ppm of other impurities was passed through a bed of LEWITAT® K2431 ion exchange resin. The MBF remaining in the eluted phenol (in ppm), at varying temperatures and flow rates in BV/hr. is given in TABLE 5. MBF was reduced to <1 ppm at all temperatures from about 114° C. to about 150° C., with the resin showing little sign of degradation above 140° C. With phenol feeds containing higher MBF content (150–160 ppm), the resin removed 80–85% MBF during the passage of about 500 bed volumes of phenol.

rities was passed through a bed of PUROLITE® CT-251 ion exchange resin. The MBF content in the eluted phenol (in ppm), at varying temperatures and flow rates in BV/hr. are given in TABLE 6. The efficiency of MBF removal increased as the temperature was raised from about 95° C. to about 147° C., but at temperatures above 140° C., the bed exhibited signs of degradation. With phenol feeds containing a higher MBF content (59–140 ppm), the efficiency at 140° C. progressively decreased from about 90% to about 50%

TABLE 5

Effect of Temperature and Flow Rates on the Removal of MBF (in ppm) from Phenol Using LEWITAT ® K2431 Ion Exchange Resin

| T (°C.) | Flow Rate, Bed Volumes/hr. | | | | | | | | |
|---|---|---|---|---|---|---|---|---|---|
| | 4.1–4.2 | 4.4–4.6 | 4.8–4.9 | 5.0–5.3 | 5.4–5.6 | 5.7–5.8 | 5.9–6.2 | 7.6 | 8.0 |
| 114 | < | | | | | | | | |
| 124–126 | | <1 | <1 | | | | | | |
| 140–142 | | <1 | | <1 | <1 | | | | |
| 145–148 | | <1 | | | | <1 | | | |
| 150 | <1 | <1 | <1 | <1 | <1 | <1 | <1 | <1 | <1 |

EXAMPLE 6

Phenol containing 39 ppm MBF, <1 ppm acetol, 138 ppm acetone, 176 ppm AMS and about 50 ppm of other impuduring the passage of about 900 bed volumes of phenol through the bed.

TABLE 6

Effect of Temperature and Flow Rates on the Removal of MBF (in ppm) from Phenol Using Purolite CT-251

| T (°C.) | MBF (Effluent) - ppm | | | | | | | |
|---|---|---|---|---|---|---|---|---|
| | 4.9 BV/hr | 5.2 BV/hr | 5.6 BV/hr | 5.8 BV/hr | 6.4 BV/hr | 6.7 BV/hr | 7.8 BV/hr | 8.1 BV/hr |
| 95–97 | 8 | | | | | 10 | | |
| 111–121 | <1 | | | | <1 | | | |
| 131–133 | | <1 | | | | | | <1 |
| 146–147 | | <1 | <1 | | | | | |
| 149–151 | | | | | | 5 | 5 | |

EXAMPLE 7

In a comparative example, phenol containing 34 ppm MBF, <1 ppm acetol, 60 ppm AMS and about 100 ppm of other impurities was passed through a bed of AMBERLYST® A-15 ion exchange resin. The MBF content in the eluted phenol (in ppm), at varying temperatures and flow rates in BV/hr. are given in TABLE 7. The efficiency of MBF removal increased as the temperature was raised from about 95° C. to about 125° C., but gradually diminished with further increase. At temperatures above 140° C., evolution of gas bubbles resulted in the cracking of the resin bed. This indicates that AMBERLYST® A-15 is not a preferred resin for the process of the present invention.

TABLE 7

Effect of Temperature and Flow Rates on the Removal of MBF (in ppm) from Phenol Using Amberlyst 15

MBF (Feed Effluent) - ppm

| T (° C.) | 3.8 BV/hr | 3.9 BV/hr | 4.0 BV/hr | 4.1 BV/hr | 4.5 BV/hr | 4.6 BV/hr | 4.7 BV/hr |
|---|---|---|---|---|---|---|---|
| 95  |      | 34/8 |      |      |      | 34/8 |       |
| 124 |      |      |      | 34/3 | 34/4 | 34/6 |       |
| 143 | 34/6 | 34/6 | 34/7 |      |      |      |       |
| 149 |      |      |      | 34/8 |      | 34/9 | 34/10 |

The preceding examples demonstrate the successful removal of methylbenzofuran from phenol using a number of aromatic sulfonic acid ion exchange resins at elevated temperatures. The process is capable of removing impurities from hundreds of bed volumes of phenol with little or no reduction in the activity of the catalyst. In the examples given, preferred ion exchange resins are AMBERLYST® 36, AMBERLYST® XE-737, PUROLITE® CT-251, and LEWITAT® K2431. More preferred resins are AMBERLYST® 36, AMBERLYST® XE-737 and LEWITAT® K2431. It will be recognized by those skilled in the art however, that the current invention is not limited to the specific examples presented above.

What is claimed is:

1. A continuous process for the reduction of methylbenzofuran impurities in a phenol stream, the process comprising the steps of;
   treating the phenol stream containing methylbenzofuran impurities to reduce the level of acetol in the phenol,
   passing the phenol stream through fixed bed containing a strong acid aromatic sulfonic acid resin at an operating temperature above about 130° C.,
   at a rate below about 12 bed volumes per hour to reduce the level of methylbenzofuran by conversion to higher boiling compounds; and
   distilling the phenol to separate phenol from higher boiling compounds.

2. A process according to claim 1, wherein the phenol is contacted with a strong acid ion exchange resin at a temperature above about 150° C.

3. A process according to claim 1, wherein the phenol is treated to reduce the level of acetol to less than 1 ppm.

4. A process according to claim 1, wherein the phenol is treated with an amine to reduce the level of acetol.

5. A process according to claim 4, wherein the level of methylbenzofuran is reduced by about 80% or more.

6. A process according to claim 5, wherein the level of methylbenzofuran is reduced to about 10 ppm or less.

7. A process according to claim 6, wherein the level of methylbenzofuran is reduced to about 3 ppm or less.

8. A process according to claim 1, wherein the phenol is contacted with the strong acid ion exchange resin at a rate below about 8 bed volumes per hour.

9. A continuous process for the reduction of methylbenzofuran impurities in phenol stream, the process comprising;
   treating the phenol stream with an amine to reduce the level of acetol in the phenol, then
   passing the phenol stream through fixed bed containing a strong acid aromatic sulfonic acid resin at an operating temperature above about 150° C.,
   at a rate below about 12 bed volumes per hour,
   wherein the level of methylbenzofuran is reduced by about 80% or more.

10. A process according to claim 9, further comprising treating the phenol with an amine to reduce the level of acetol in the phenol to less than 1 ppm, then
    passing the phenol through a fixed resin bed containing an aromatic sulfonic acid resin at a rate below about 8 bed volumes per hour,
    wherein the level of methylbenzofuran is reduced to about 10 ppm or less.

11. A process according to claim 10, wherein the level of methylbenzofuran is reduced to about 3 ppm or less.

* * * * *